US00PP16855P3

(12) United States Plant Patent
Olesen

(10) Patent No.: US PP16,855 P3
(45) Date of Patent: Jul. 25, 2006

(54) MINIATURE ROSE PLANT NAMED 'POULPAR030'

(50) Latin Name: ***Rosa* hybrid**
Varietal Denomination: Poulpar030

(75) Inventor: Mogens Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 143 days.

(21) Appl. No.: 11/002,745

(22) Filed: Dec. 1, 2004

(65) Prior Publication Data

US 2006/0117426 P1 Jun. 1, 2006

(51) Int. Cl.
*A01H 5/00* (2006.01)

(52) U.S. Cl. ..... Plt./116

(58) Field of Classification Search ..... Plt./116, Plt./118, 119, 120

See application file for complete search history.

*Primary Examiner*—Anne Marie Grunberg
*Assistant Examiner*—June Hwu

(57) ABSTRACT

A new miniature rose plant that has abundant, apricot flowers and attractive foliage. The variety successfully propagates from softwood cuttings and is suitable for year-round production in commercial glasshouses. This new and distinct variety has shown to be uniform and stable in the resulting generations from asexual propagation.

1 Drawing Sheet

Botanical classification: *Rosa* hybrid.
Variety denomination: 'Poulpar030'.

SUMMARY OF THE INVENTION

The present invention constitutes a new and distinct variety of miniature rose plant which originated from a controlled crossing between the female parent, 'KORkleiva' described and illustrated in U.S. Plant Pat. No. 11,232, issued Feb. 22, 2000, and the male pollen parent, an unnamed seedling. The two parents were crossed, and the resulting seeds were planted in a controlled environment. The new variety is named 'Poulpar030'.

The new rose may be distinguished from its female parent by the following combination of characteristics:

1. Petal count of 'Poulpar030' is 25 petals. The seed parent has 25 to 30 petals.
2. 'Poulpar030' has apricot flowers, whereas the seed parent has light yellow flowers.

The new variety may be distinguished from pollen parent by the following combination of characteristics:

1. Petal count of 'Poulpar030' is 25 petals. The pollen parent has 50 petals.
2. 'Poulpar030' has apricot flowers, while the pollen parent has orange flowers.

The objective of the hybridization of this rose variety for commercial culture was to create a new and distinct variety with unique qualities, such as:

1. Uniform and abundant apricot flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventors, and distinguish 'Poulpar030' from all other varieties of which we are aware.

As part of the rose development program, Mogens N. Olesen germinated the seeds from the aforementioned hybridization and conducted evaluations on the resulting seedlings in a controlled environment in Fredensborg, Denmark.

'Poulpar030' was selected by the inventor as a single plant from the progeny of the hybridization in 2001.

Asexual reproduction of 'Poulpar030' by cuttings and traditional budding was first done by Mogens N. Olesen in the nursery in Fredensborg, Denmark in April 2002. This initial and other subsequent propagations conducted in controlled environments have demonstrated that the characteristics of 'Poulpar030' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'Poulpar030'. Specifically illustrated in the drawing:

FIG. 1.1; Open flower, viewed from above, and open flower showing attachment to receptacle and pedicel;

FIG. 1.2; Flower buds closed and partially open;

FIG. 1.3; Sepals;

FIG. 1.4; Flower petals, detached;

FIG. 1.5; Reproductive organs, sepals and pedicel;

FIG. 1.6; Mature leaves;

FIG. 1.7; Juvenile leaf;

FIG. 1.8; Bare stem.

DETAILED DESCRIPTION OF THE VARIETY

The following is a description of 'Poulpar030', as observed in its growth in glasshouses in Burlington, Canada. Observed plants are 4 months of age and were cultivated in 10.5 cm pots. Color references are made using The Royal Horticultural Society (London, England) Colour Chart, 2001, except where common terms of color are used.

For a comparison, several physical characteristics of the rose variety 'Poulnil', a rose variety from the same inventor described and illustrated in U.S. Plant Pat. No. 13,301 and issued on Dec. 3, 2002, are compared to 'Poulpar030' in Chart 1.

CHART 1

| | 'Poulpar030' | 'Poulnil' |
|---|---|---|
| Petalage. | Semi-double; 25 petals. | Semi-double; 16 to 19 petals. |
| Bud color as sepals unfold. | Yellow Group 13A with intonations of Orange-Red Group 30A and Orange-Red Group 34A. | Orange-Red Group 31A/B. |
| Flower diameter. | 60 mm. | 65 to 75 mm. |

FLOWER AND FLOWER BUD

Blooming habit: Continuous.

Flower bud:

*Size.*—Upon opening, 22 mm in length from base of receptacle to end of bud. 12 mm in diameter.

*Bud form.*—Ovate.

*Bud color.*—As sepals unfold, Yellow Group 13A with intonations of Orange-Red Group 30A and 34A.

*Sepals.*—Upper Surface: Color: Yellow-Green Group 147A. Surface: Weak pubescence observed. Lower Surface: Color: Yellow-Green Group 147B. Texture: Few stipitate glands. Shape: Normally cirrhose at the apex occasionally sepals exhibit very strong foliaceous appendages causing sepal shape to be irregular. Margins: Margins have strong foliaceous appendages on three of the five sepals. Size: 30 mm (l) by 14 mm (w).

*Receptacle.*—Surface Texture: Smooth. Shape: Funnel shaped. Size: 5 mm (h)×5 mm (w). Color: Yellow-Green Group 144A. Anthocyanin: None observed.

*Pedicel.*—Surface: Somewhat rough with small prickles. Length: 60 mm average. Diameter: 3 mm. Color: Yellow-Green Group 144A. Strength: Strong.

*Borne.*—Singularly.

Flower bloom:

*Fragrance.*—Moderate floral scent.

*Duration.*—Flowers last up to 20 to 25 days. Petals fall cleanly away from plant after flowers have fully matured.

*Size.*—Average flower diameter is 60 mm when open. Depth is 20 mm.

*Form.*—As flowers open, petals are held in a tight pointed center. Flowers open to form a rosette with overlapping, slightly reflexed petals.

*Shape of flower when viewed from the side.*—Upon opening, upper part: Flat. Upon opening, lower part: Flat. Open flower, upper part: Flattened convex. Open flower, lower part: Flattened convex.

Petalage: 25 petals, 5 of which are petaloids.

Color:

*Upon opening, petals.*—Outermost petals: Upper Surface: Yellow-Orange Group 14C. Lower Surface: Orange Group 26A to 26C with Yellow Group 8A. Innermost petals: Upper Surface: Yellow-Orange Group 14C. Lower Surface: Orange Group 26A to 26C with underlying intonations of Yellow Group 8A.

*Upon opening, basal petal spots.*—Upper surface: None. Lower Surface: Yellow Group 8A.

*After opening, petals.*—Outermost and Innermost petals: Upper Surface: Yellow Group 12D at middle and marginal zones. Petal margins have a thin band of Orange Group 27A. Lower Surface: Underlying intonations of Yellow-Orange Group 18A with overlay of Orange Group 26A. Margins have intonations of Red Group 39B.

*After opening, basal petal spots.*—Outermost and Innermost petals: Upper Surface: Yellow Group 7B. Lower Surface: Yellow Group 7B to 1C.

Gernal tonality: On open flower Yellow-Orange Group 20B with intonations of Orange Group 25B. No change in the general tonality at the end of the $10^{th}$ day. Afterwards, general tonality is Orange Group 27C with intonations of Red Group 36A.

Petals:

*Petal reflex.*—Somewhat reflexed.

*Petal margin.*—Entire and uniform undulations of margin observed.

*Shape.*—Narrow elliptical to orbicular. Base: Acute and obtuse. Apex: Rounded.

*Size.*—On average, 31 (l)×30 mm (w).

*Texture.*—Smooth.

*Thickness.*—Average.

*Arrangement.*—Not formal.

Petaloids:

*Quantity.*—5.

*Size.*—16 mm (l)×10 mm (w).

*Shape.*—Narrow elliptical and irregular. Base is acute and apex is round.

*Color.*—Upper surface: Yellow Group 12D at middle and marginal zones. Petal margins have a thin band of Orange Group 27A. Lower Surface: Underlying intonations of Yellow-Orange Group 18A with overlay of Orange Group 26A. Margins have intonations of Red Group 39B.

Reproductive organs:

*Pollen.*—None observed.

*Anthers.*—Size: 2 mm long. Color: Yellow Group 8B. Quantity: 53.

*Filaments.*—Color: Yellow Group 6B. Length: 4 mm.

*Pistils.*—Length: 9 mm. Quantity: 30.

*Stigmas.*—Superior relative to the length of the filaments and the height of the anthers. Color: Yellow Group 8C.

*Styles.*—Color: Yellow Group 8C to White Group 155A.

*Seed formation.*—None observed.

PLANT

Plant growth: Moderate, upright to bushy. When grown as a 10 cm pot plant on its own roots, the average height of the plant itself is 21 cm and the average width is 13 cm.

Stems:

*Color.*—Young wood: Yellow-Green Group 144A. Older wood: Yellow-Green Group 144A.

*Diameter.*—2.5 mm.

*Internodal distance.*—20 mm.

*Length of stems.*—On average canes are 20 cm from the base of the stem to the flowering portion.

*Surface texture.*—Young wood: Smooth. Older wood: Smooth.

Thorns:

*Incidence.*—10 per 10 cm of stem.

*Color.*—Mature and juvenile thorns are Greyed-Red Group 181A.

*Shape.*—Flat.

Plant foliage: Normal number of leaflets on normal leaves in middle of the stem: 5 leaflets.

*Compound leaf size.*—80 mm (l)×55 mm (w).

*Quantity.*—5 leaves per 10 cm of stem.

*Color.*—Juvenile foliage: Upper Leaf Surface: Yellow-Green Group 146A with margins Greyed-Purple Group 183A. Lower Leaf Surface: Yellow-Green Group 147B to 147C with Greyed-Purple Group 184A at random. Mature foliage: Upper Leaf Surface: Yellow-Green Group 147A to Green Group 138A. Lower Leaf Surface: Green Group 138B.

Plant leaves and leaflets:

*Stipules.*—Size: 7 mm. Shape: Linear, slightly broad based with outward extending apecies. Margins: Entire with many stipitate glands. Color: Green Group 138A.

*Petiole.*—Length: 15 mm. Diameter: 2 mm. Color: Upper surface: Yellow-Green Group 146B with intonations of Greyed-Purple Group 178A. Lower surface: Yellow-Green Group 146C. Underneath: Numerous small prickles observed. Numerous stipitate glands observed.

*Rachis.*—Size: 29 mm. Color: Yellow-Green Group 146B with intonations of Greyed-Purple Group 178A. Undeneath: Small prickles observed. Numerous stipitate glands observed.

*Leaflet.*—Size: 43 mm (l)×31 mm (w). Edge: Doubly serrated. General Shape: Ovate. Apex Shape: Cuspidate. Base Shape: Rounded. Texture: Smooth. Thickness: Average to thin. Arrangement: Odd pinnate. Venation: Reticulate. Leaf Gloss: Matte finish.

Disease resistance: Average resistance to powdery and downy mildews, black spot, and *Botrytis* under normal growing conditions in Burlington, Canada, and Fredensborg, Denmark.

What is claimed:

1. A new and distinct variety of rose plant of the miniature class named 'Poulpar030', substantially as illustrated and described herein, due to its abundant apricot flowers, vigorous growth, compact habit, suitability for production from softwood cuttings in pots, and durable flowers and foliage that make the variety suitable for distribution in the floral industry.

* * * * *

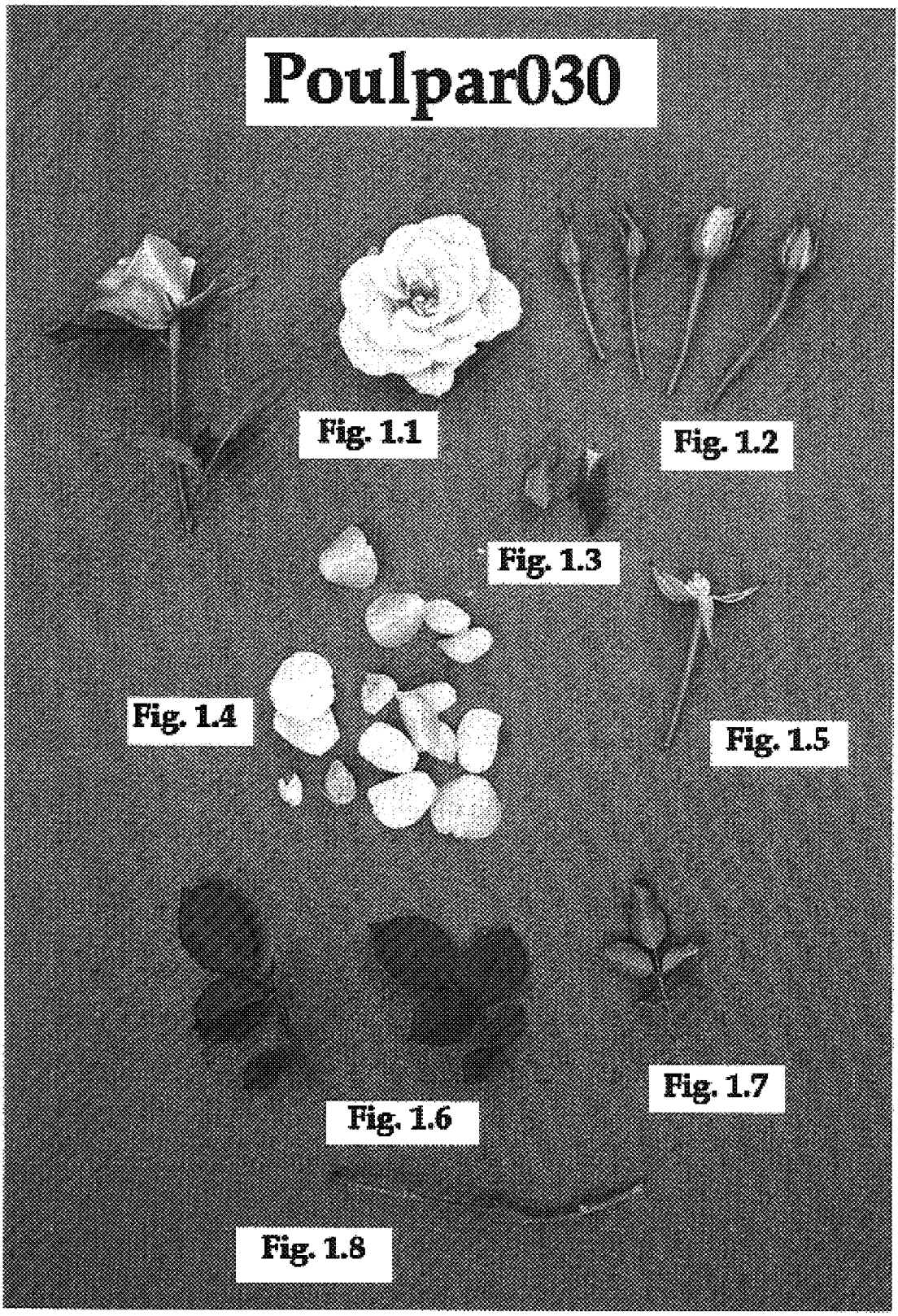
Poulpar030
Fig. 1.1
Fig. 1.2
Fig. 1.3
Fig. 1.4
Fig. 1.5
Fig. 1.6
Fig. 1.7
Fig. 1.8